(12) United States Patent
Ueda

(10) Patent No.: US 10,737,457 B2
(45) Date of Patent: Aug. 11, 2020

(54) MEDICAL STERILE COVER AND MEDICAL OBSERVATION APPARATUS

(71) Applicant: Sony Olympus Medical Solutions Inc., Tokyo (JP)

(72) Inventor: Masaaki Ueda, Kanagawa (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 121 days.

(21) Appl. No.: 15/923,086

(22) Filed: Mar. 16, 2018

(65) Prior Publication Data
US 2018/0296293 A1   Oct. 18, 2018

(30) Foreign Application Priority Data

Apr. 13, 2017   (JP) ................. 2017-080008

(51) Int. Cl.
| | | |
|---|---|---|
| *B32B 1/02* | (2006.01) | |
| *A61B 46/10* | (2016.01) | |
| *A61B 90/50* | (2016.01) | |
| *A61B 90/25* | (2016.01) | |
| *A61B 90/00* | (2016.01) | |
| *A61B 46/00* | (2016.01) | |
| *A61B 90/20* | (2016.01) | |

(52) U.S. Cl.
CPC ................ *B32B 1/02* (2013.01); *A61B 46/10* (2016.02); *A61B 46/40* (2016.02); *A61B 90/25* (2016.02); *A61B 90/36* (2016.02); *A61B 90/50* (2016.02); *A61B 90/20* (2016.02); *A61B 2090/037* (2016.02); *A61B 2090/373* (2016.02)

(58) Field of Classification Search
CPC ........... B32B 1/08; A61B 46/10; A61B 46/40; A61B 90/20; A61B 90/25; A61B 90/36
See application file for complete search history.

(56) References Cited

FOREIGN PATENT DOCUMENTS

JP   2016-7233   1/2016

*Primary Examiner* — Walter Aughenbaugh
(74) *Attorney, Agent, or Firm* — XSENSUS LLP

(57) ABSTRACT

There is provided a medical sterile cover including: a layered structure in which a plurality of covering members that cover a medical observation apparatus to ensure a sterile state of the medical observation apparatus is layered; and a detachment section configured to detach the layered plurality of covering members layer by layer.

11 Claims, 9 Drawing Sheets

MEDICAL STERILE COVER AND MEDICAL OBSERVATION APPARATUS

CROSS REFERENCE TO RELATED APPLICATIONS

This application claims the benefit of Japanese Priority Patent Application JP 2017-080008 filed Apr. 13, 2017, the entire contents of which are incorporated herein by reference.

BACKGROUND

The present disclosure relates to a medical sterile cover and a medical observation apparatus.

Recently, in the medical field, to support microsurgery such as neurosurgical procedures, for example, medical observation apparatus capable of enlarged observation of an observation target such as an affected area are used in some cases. Examples of medical observation apparatus include a medical observation apparatus provided with an optical microscope, and a medical observation apparatus provided with an imaging device that functions as an electronic imaging microscope. In the following, the above medical observation apparatus provided with an optical microscope will be designated an "optical medical observation apparatus". Also, in the following, the above medical observation apparatus provided with an imaging device will be designated an "electronic imaging medical observation apparatus" or simply a "medical observation apparatus" in some cases.

Also, to ensure a sterile state, optical medical observation apparatus and electronic imaging medical observation apparatus are often used while being covered by a medical sterile cover called a drape. In these circumstances, technology related to medical sterile covers is being developed. Examples of the above technology include the technology described in JP 2016-7233A.

SUMMARY

As described above, to ensure a sterilized state, optical medical observation apparatus and electronic imaging medical observation apparatus are often used while being covered by a medical sterile cover. In optical medical observation apparatus and electronic imaging medical observation apparatus, the part covered by the medical sterile drape becomes a region (hereinafter designated the "sterile region") where a sterile state is ensured.

If a site whose sterile state is not ensured, such as the face or head of a medical personnel member, comes into contact with a part covered by an existing medical sterile cover, like the medical sterile cover described in JP 2016-7233A, for example, the medical personnel member may need to re-cover the optical medical observation apparatus or electronic imaging medical observation apparatus with a new medical sterile cover. If a situation of re-covering with a new medical sterile cover like the above occurs, surgery is interrupted temporarily, which leads to reduced surgical efficiency. Additionally, increased costs due to the use of a new medical sterile cover are a concern.

The present disclosure proposes a novel and improved medical sterile cover and medical observation apparatus in which, in the case in which a site whose sterile state is not ensured on a medical personnel member comes into contact with the medical sterile cover, a more rapid return to a sterile state is realizable.

According to an embodiment of the present disclosure, there is provided a medical sterile cover including: a layered structure in which a plurality of covering members that cover a medical observation apparatus to ensure a sterile state of the medical observation apparatus is layered; and a detachment section configured to detach the layered plurality of covering members layer by layer.

In addition, according to an embodiment of the present disclosure, there is provided a medical observation apparatus including: an arm including a plurality of links joined to each other by one or a plurality of joint sections; an imaging device supported by the arm; and a medical sterile cover. The medical sterile cover includes a layered structure in which a plurality of covering members that cover the imaging device and at least a portion of the arm to ensure a sterile state of the covered part is layered, and a detachment section configured to detach the layered plurality of covering members layer by layer.

According to an embodiment of the present disclosure, in the case in which a site whose sterile state is not ensured on a medical personnel member comes into contact with the medical sterile cover, a more rapid return to a sterile state can be realized.

Note that the effects described above are not necessarily limitative. With or in the place of the above effects, there may be achieved any one of the effects described in this specification or other effects that may be grasped from this specification.

DETAILED DESCRIPTION OF THE EMBODIMENT(S)

Figure 1:
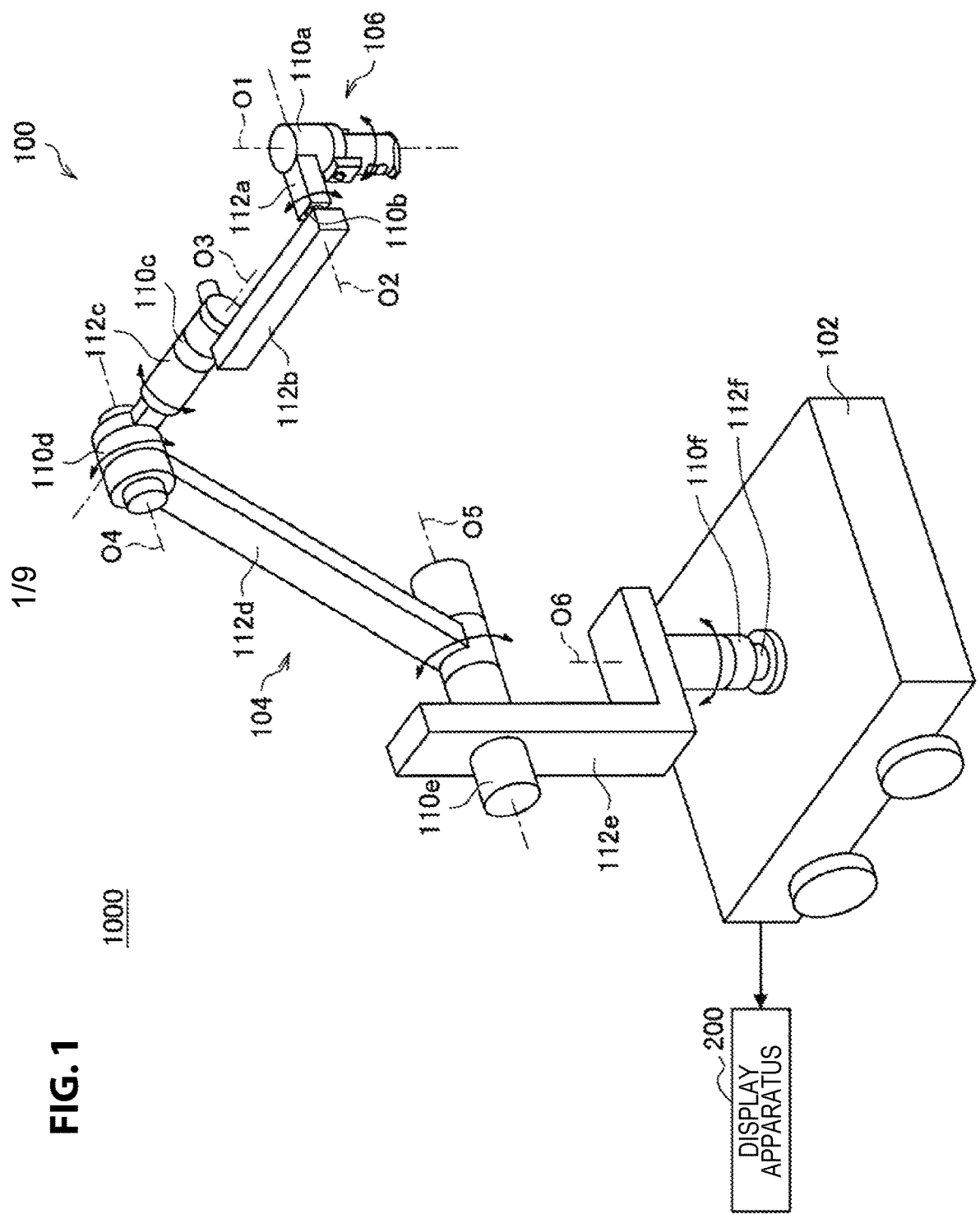
FIG. 1 is an explanatory diagram illustrating an example of a configuration of a medical observation system according to the present embodiment.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

The description hereinafter will proceed in the following order.

1. Medical observation system according to present embodiment
2. Medical sterile cover according to present embodiment

[1] Medical Observation System

First, before describing an example of the configuration of a medical sterile cover according to the present embodiment, an example of a medical observation system according to the present embodiment that includes a medical observation apparatus in which the medical sterile cover is used according to the present embodiment will be described.

Note that although the following mainly gives an example of a case in which the medical observation apparatus according to the present embodiment is an electronic imaging medical observation apparatus, the medical observation apparatus according to the present embodiment is not limited to an electronic imaging medical observation apparatus. For example, the medical observation apparatus according to the present embodiment may also be an optical medical observation apparatus.

FIG. 1 is an explanatory diagram illustrating an example of the configuration of a medical observation system 1000 according to the present embodiment. The medical observation system 1000 includes a medical observation apparatus 100 and a display apparatus 200, for example.

Note that the medical observation system according to the present embodiment is not limited to the example illustrated in FIG. 1.

For example, the medical observation system according to the present embodiment additionally may include a control apparatus (not illustrated) that controls various operations in the medical observation apparatus 100. In the medical observation system 1000 illustrated in FIG. 1, as described later, an example is illustrated in which, by providing the medical observation apparatus 100 with a control section (described later) that performs processes according to the state notification method according to the present embodiment, the medical observation apparatus 100 includes the functions of the control apparatus (not illustrated).

Examples of the control apparatus (not illustrated) include arbitrary equipment capable of performing processes according to the state notification method according to the present embodiment, such as a "medical controller" and a "computer such as a server". Also, the control apparatus (not illustrated) may be, for example, an integrated circuit (IC) that can be embedded in equipment like the above.

Additionally, the medical observation system according to the present embodiment may also be a configuration that includes multiple medical observation apparatuses 100 and display apparatuses 200. In the case of including multiple medical observation apparatuses 100, in each medical observation apparatus 100, processes according to the state notification method in the medical observation apparatus 100 described later are performed. Also, in the case in which the medical observation system according to the present embodiment is a configuration that includes multiple medical observation apparatuses 100 and display apparatuses 200, the medical observation apparatus 100 and the display apparatus 200 may be associated in a 1-to-1 manner, or multiple medical observation apparatuses 100 may be associated with a single display apparatus 200. In the case in which multiple medical observation apparatuses 100 are associated with a single display apparatus 200, which medical observation apparatus 100 provides a taken image to be displayed on a display screen is switched by performing a switching operation or the like in the display apparatus 200, for example.

Figure 2:
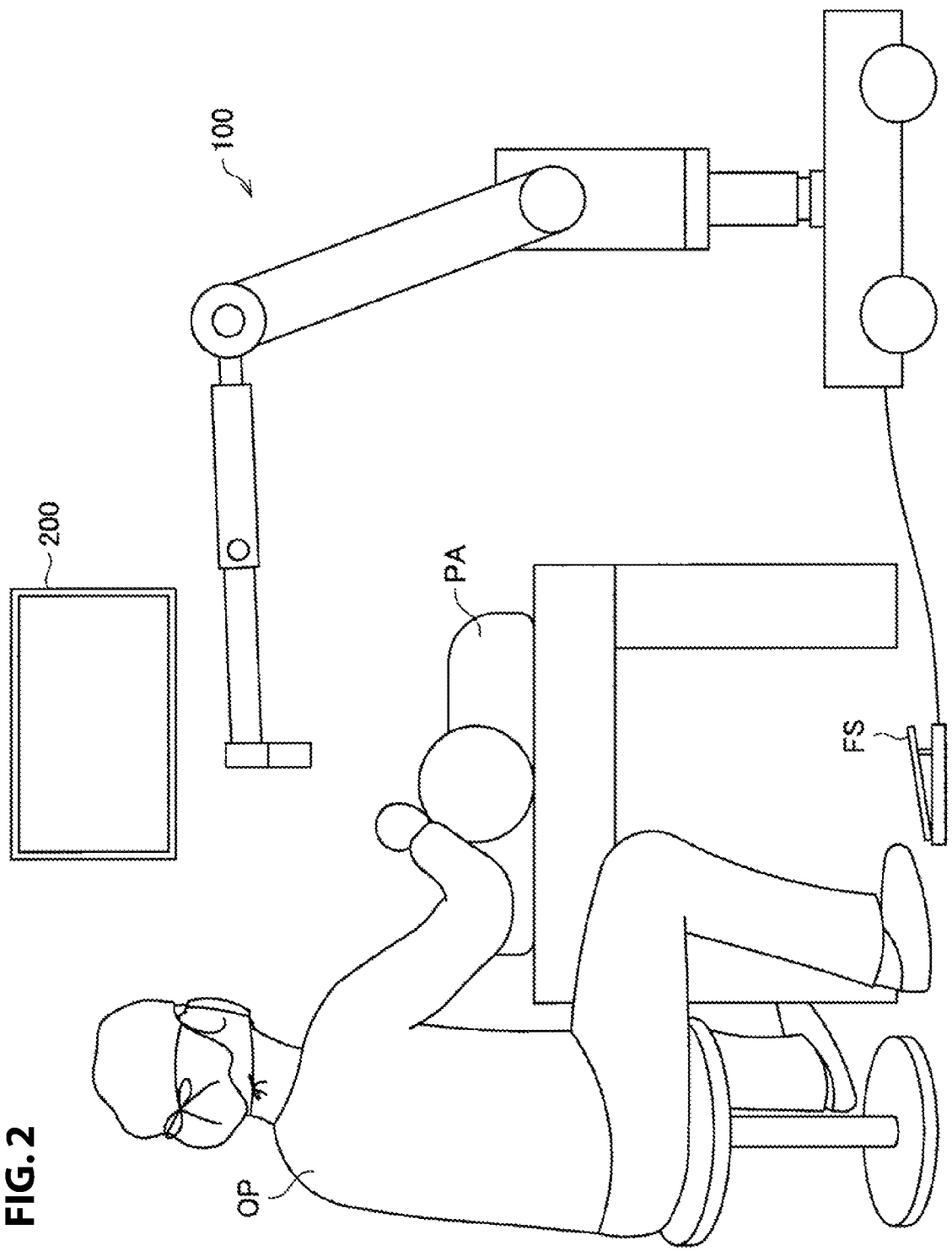
FIG. 2 is an explanatory diagram illustrating an example of a use case in which the medical observation system according to the present embodiment is used.

FIG. 2 is an explanatory diagram illustrating an example of a use case in which the medical observation system 1000 according to the present embodiment is used.

By an imaging device (described later) provided in the medical observation apparatus 100, an observation target patient PA (a patient who undergoes a medical procedure) is imaged. In the following, a captured image captured by the medical observation apparatus according to the present embodiment, such as a captured image that captures the above patient who undergoes a medical procedure, is designated a "medical captured image".

The medical captured image captured in the medical observation apparatus 100 is displayed on a display screen of a display apparatus 200. Subsequently, a surgeon OP (an example of a user of the medical observation apparatus 100) who performs a medical procedure by using the medical observation apparatus 100 performs the medical procedure on the patient PA while looking at the medical captured image displayed on the display screen of the display apparatus 200.

Also, the surgeon OP operates an operating device external to the medical observation apparatus 100, such as a footswitch FS, or an operating device (described later) provided in the medical observation apparatus 100, thereby causing an arm (described later) and the imaging device (described later) provided in the medical observation apparatus 100 to operate, and putting the medical observation apparatus 100 into a desired state.

Hereinafter, each apparatus included in the medical observation system 1000 will be described.

[1-1] Display Apparatus 200

The display apparatus 200 is a display device in the medical observation system 1000, and corresponds to an external display device from the perspective of the medical observation apparatus 100. The display apparatus 200 displays various images on a display screen, such as a medical captured image (a moving image or multiple still images; the same applies hereinafter) taken in the medical observation apparatus 100, or an image related to a user interface (UI), for example. In addition, the display apparatus 200 may also be a configuration capable of 3D display. The display on the display apparatus 200 is controlled by, for example, the medical observation apparatus 100 or the control apparatus (not illustrated).

In the medical observation system 1000, the display apparatus 200 is installed in an arbitrary location visible to a person involved in a surgery inside an operating room, such as on a wall, the ceiling, or the floor of the operating room, for example. Examples of the display apparatus 200 include a liquid crystal display, an organic electro-luminescence (EL) display, a cathode ray tube (CRT) display, and the like.

Note that the display apparatus 200 is not limited to the example illustrated above.

For example, the display apparatus 200 may also be an arbitrary wearable apparatus that is used by being worn on the body of the surgeon or the like, such as a head-mounted display, an eyewear-type apparatus, or the like.

The display apparatus 200 runs on electric power supplied from an internal power source such as a battery provided in the display apparatus 200, on electric power supplied from a connected external power source, or the like, for example.

[1-2] Medical Observation Apparatus 100

The medical observation apparatus 100 is an electronic imaging medical observation apparatus. For example, in the case in which the medical observation apparatus 100 is used during surgery, the surgeon (one example of the user of the medical observation apparatus 100) observes an operating site while referring to a medical captured image which has been taken by the medical observation apparatus 100 and displayed on the display screen of the display apparatus 200, and performs various treatments, such as techniques depending on the surgical procedure, on the operating site.

First, FIG. 1 will be referenced to describe an example of a hardware configuration of the medical observation apparatus 100.

The medical observation apparatus 100 is provided with a base 102, an arm 104, an imaging device 106, and sensors (a sensor group), for example.

Additionally, although not illustrated in FIG. 1, the medical observation apparatus 100 may also be provided with, for example, one or multiple processors (not illustrated) including a computational circuit such as a microprocessing unit (MPU), read-only memory (ROM; not illustrated), random access memory (RAM; not illustrated), a recording medium (not illustrated), and a communication device (not illustrated). The medical observation apparatus 100 runs on electric power supplied from an internal power source such as a battery provided in the medical observation apparatus 100, on electric power supplied from a connected external power source, or the like, for example.

The one or multiple processors (not illustrated) function as the control section described later. The ROM (not illustrated) stores programs and control data such as computational parameters used by the one or multiple processors (not illustrated). The RAM (not illustrated) temporarily stores programs executed by the one or multiple processors (not illustrated), or the like.

The recording medium (not illustrated) functions as a storage section described later. A variety of data is stored on the recording medium (not illustrated), including data related to the state notification method according to the present embodiment, such as data indicating a first threshold value (described later) and data indicating a second threshold value (described later), and various applications, for example. Herein, examples of the recording medium (not illustrated) include a magnetic recording medium such as a hard disk, non-volatile memory such as flash memory, and the like. Additionally, the recording medium (not illustrated) may also be removable from the medical observation apparatus 100.

The communication device (not illustrated) is a communication device provided in the medical observation apparatus 100, and fulfills a role of communicating in a wireless or wired manner with an external apparatus such as the display apparatus 200. Herein, examples of the communication device (not illustrated) include an IEEE 802.15.1 port and transmitting-receiving circuit (wireless communication), an IEEE 802.11 port and transmitting-receiving circuit (wireless communication), a communication antenna and a radio frequency (RF) circuit (wireless communication), a local area network (LAN) terminal and a transmitting-receiving circuit (wired communication), and the like.

[1-2-1] Base 102

The base 102 is the base of the medical observation apparatus 100. One end of the arm 104 is connected to the base 102, and the base 102 supports the arm 104 and the imaging device 106.

Also, casters are provided on the base 102, for example, and the medical observation apparatus 100 contacts the floor through the casters. By providing the casters, the medical observation apparatus 100 is able to move easily over the floor by the casters.

[1-2-2] Arm 104

The arm 104 includes multiple links joined to each other by joint sections.

In addition, the arm 104 supports the imaging device 106. The imaging device 106 supported by the arm 104 is movable three-dimensionally, and after moving, the position and the attitude of the imaging device 106 are maintained by the arm 104.

More specifically, the arm 104 includes, for example, multiple joint sections 110a, 110b, 110c, 110d, 110e, and 110f, and multiple links 112a, 112b, 112c, 112d, 112e, and 112f rotatably joined to each other by the joint sections 110a, 110b, 110c, 110d, 110e, and 110f. The rotatable range of each of the joint sections 110a, 110b, 110c, 110d, 110e, and 110f is set arbitrarily during the design stage, the manufacturing stage, or the like so that the desired motion of the arm 104 is realized.

In other words, in the medical observation apparatus 100 illustrated in FIG. 1, six degrees of freedom are realized in relation to the movement of the imaging device 106 by six rotation axes (first axis O1, second axis O2, third axis O3, fourth axis O4, fifth axis O5, and sixth axis O6) corresponding to the six joint sections 110a, 110b, 110c, 110d, 110e, and 110f included in the arm 104. More specifically, in the medical observation apparatus 100 illustrated in FIG. 1, motion with six degrees of freedom, including three degrees of translational freedom and three degrees of rotational freedom, is realized.

Actuators (not illustrated) are provided in each of the joint sections 110a, 110b, 110c, 110d, 110e, and 110f. Each of the joint sections 110a, 110b, 110c, 110d, 110e, and 110f rotates about the corresponding rotation axis by the driving of the actuators (not illustrated). The driving of the actuators (not illustrated) is controlled by, for example, a processor that functions as the control section described later, or an external control apparatus (not illustrated).

By having each of the joint sections 110a, 110b, 110c, 110d, 110e, 110f rotate about the corresponding rotation axis by the driving of the actuators (not illustrated), various operations of the arm 104, such as extending and contracting (folding up) the arm 104, for example, are realized.

The joint section 110a has an approximately cylindrical shape, and supports the imaging device 106 (the top end of the imaging device 106 in FIG. 1) on the front end portion of the joint section 110a (the bottom end portion in FIG. 1), so as to allow revolution about a rotation axis (first axis O1) parallel to the central axis of the imaging device 106. Herein, the medical observation apparatus 100 is configured so that the first axis O1 is aligned with the optical axis in the imaging device 106. In other words, by causing the imaging device 106 to revolve about the first axis O1 illustrated in FIG. 1, the medical captured image captured by the imaging device 106 becomes an image which has changed so that the field of view rotates.

The link 112a is an approximately rod-shaped member, and securely supports the joint section 110a. The link 112a extends in a direction orthogonal to the first axis O1, for example, and is connected to the joint section 110b. The joint section 110b has an approximately cylindrical shape, and supports the link 112a so as to allow revolution about a rotation axis (second axis O2) orthogonal to the first axis O1. Also, the link 112b is securely connected to the joint section 110b.

The link 112b is an approximately rod-shaped member, and extends in a direction orthogonal to the second axis O2. Also, each of the joint section 110b and the joint section 110c is connected to the link 112b.

The joint section 110c has an approximately cylindrical shape, and supports the link 112b so as to allow revolution about a rotation axis (third axis O3) mutually orthogonal to each of the first axis O1 and the second axis O2. Also, one end of the link 112c is securely connected to the joint section 110c.

Herein, by having the front end side (the side on which the imaging device 106 is provided) of the arm 104 revolve about the second axis O2 and the third axis O3, the imaging device 106 can be made to move so that the position of the imaging device 106 in the horizontal plane is changed. In other words, in the medical observation apparatus 100, controlling the rotation about the second axis O2 and the third axis O3 makes it possible to move the field of view of the medical captured image in a flat plane.

The link 112c is a member in which one end has an approximately cylindrical shape, and the other end has an approximately rod-like shape. On the side of the one end of the link 112c, the joint section 110c is securely connected so that the central axis of the joint section 110c and the central axis of the approximately cylindrical shape are the same. Also, on the side of the other end of the link 112c, the joint section 110d is connected.

The joint section 110d has an approximately cylindrical shape, and supports the link 112c so as to allow revolution about a rotation axis (fourth axis O4) orthogonal to the third axis O3. The link 112d is securely connected to the joint section 110d.

The link 112d is an approximately rod-shaped member, and extends orthogonally to the fourth axis O4. One end of the link 112d is securely connected to the joint section 110d so as to abut the approximately cylindrical side face of the joint section 110d. Also, the joint section 110e is connected to the other end of the link 112d (the end on the opposite side of the side where the joint section 110d is connected).

The joint section 110e has an approximately cylindrical shape, and supports one end of the link 112d so as to allow revolution about a rotation axis (fifth axis O5) parallel to the fourth axis O4. Also, one end of the link 112e is securely connected to the joint section 110e.

Herein, the fourth axis O4 and the fifth axis O5 are rotation axis about which the imaging device 106 may be moved in the vertical direction. By having the front end side (the side on which the imaging device 106 is provided) of the arm 104 revolve about the fourth axis O4 and the fifth axis O5, the position of the imaging device 106 in the vertical direction changes. Thus, by having the front end side (the side on which the imaging device 106 is provided) of the arm 104 revolve about the fourth axis O4 and the fifth axis O5, changing the distance between the imaging device 106 and an observation target, such as an operating site of a patient, becomes possible.

The link 112e is a member that includes a combination of a first member having an approximate L-shape with one edge extending in the vertical direction while the other edge extends in the horizontal direction, and a rod-like second member that extends vertically downward from the part of the first member that extends in the horizontal direction. The joint section 110e is securely connected to the part of the first member of the link 112e that extends in the vertical direction. Also, the joint section 110f is connected to the second member of the link 112e.

The joint section 110f has an approximately cylindrical shape, and supports the link 112e so as to allow revolution about a rotation axis (sixth axis O6) parallel to the vertical direction. Also, the link 112f is securely connected to the joint section 110f.

The link 112f is an approximately rod-shaped member, and extends in the vertical direction. The joint section 110f is connected to one end of the link 112f. Also, the other end of the link 112f (the end on the opposite side of the side where the joint section 110f is connected) is securely connected to the base 102.

By having the arm 104 include the configuration indicated above, in the medical observation apparatus 100, six degrees of freedom are realized with respect to the movement of the imaging device 106.

Note that the configuration of the arm 104 is not limited to the example indicated above.

For example, each of the joint sections 110a, 110b, 110c, 110d, 110e, and 110f of the arm 104 may be provided with a brake that restrains rotation in each of the joint sections 110a, 110b, 110c, 110d, 110e, and 110f. The brake according to the present embodiment may be a brake of an arbitrary method, such as a mechanically driven brake or an electrically driven electromagnetic brake, for example.

The driving of the above brakes is controlled by, for example, a processor that functions as the control section described later, or an external control apparatus (not illustrated). By controlling the driving of the above brakes, in the medical observation apparatus 100, the operating mode of the arm 104 is set. Examples of operating modes of the arm 104 include a locked mode and a free mode.

Herein, the locked mode according to the present embodiment is, for example, an operating mode in which the position and the attitude of the imaging device 106 are locked by using brakes to restrain rotation about each rotation axis provided in the arm 104. By having the arm 104 enter the locked mode, the operating state of the medical observation apparatus 100 becomes a locked state in which the position and the attitude of the imaging device 106 are locked.

Also, the free mode according to the present embodiment is an operating mode in which the above brakes are released, thereby allowing each rotation axis provided in the arm 104 to rotate freely. For example, in the free mode, the position and the attitude of the imaging device 106 are adjustable by direct operations performed by the surgeon. Herein, a direct operation according to the present embodiment means, for example, an operation in which the surgeon grips the imaging device 106 with his or her hand, and directly moves the imaging device 106.

[1-2-3] Imaging Device 106

The imaging device 106 is supported by the arm 104, and images an observation target such as an operating site of a patient, for example. Imaging in the imaging device 106 is controlled by, for example, a processor that functions as the control section described later, or an external control apparatus (not illustrated).

The imaging device 106 has a configuration corresponding to an electronic imaging microscope, for example.

Figure 3:
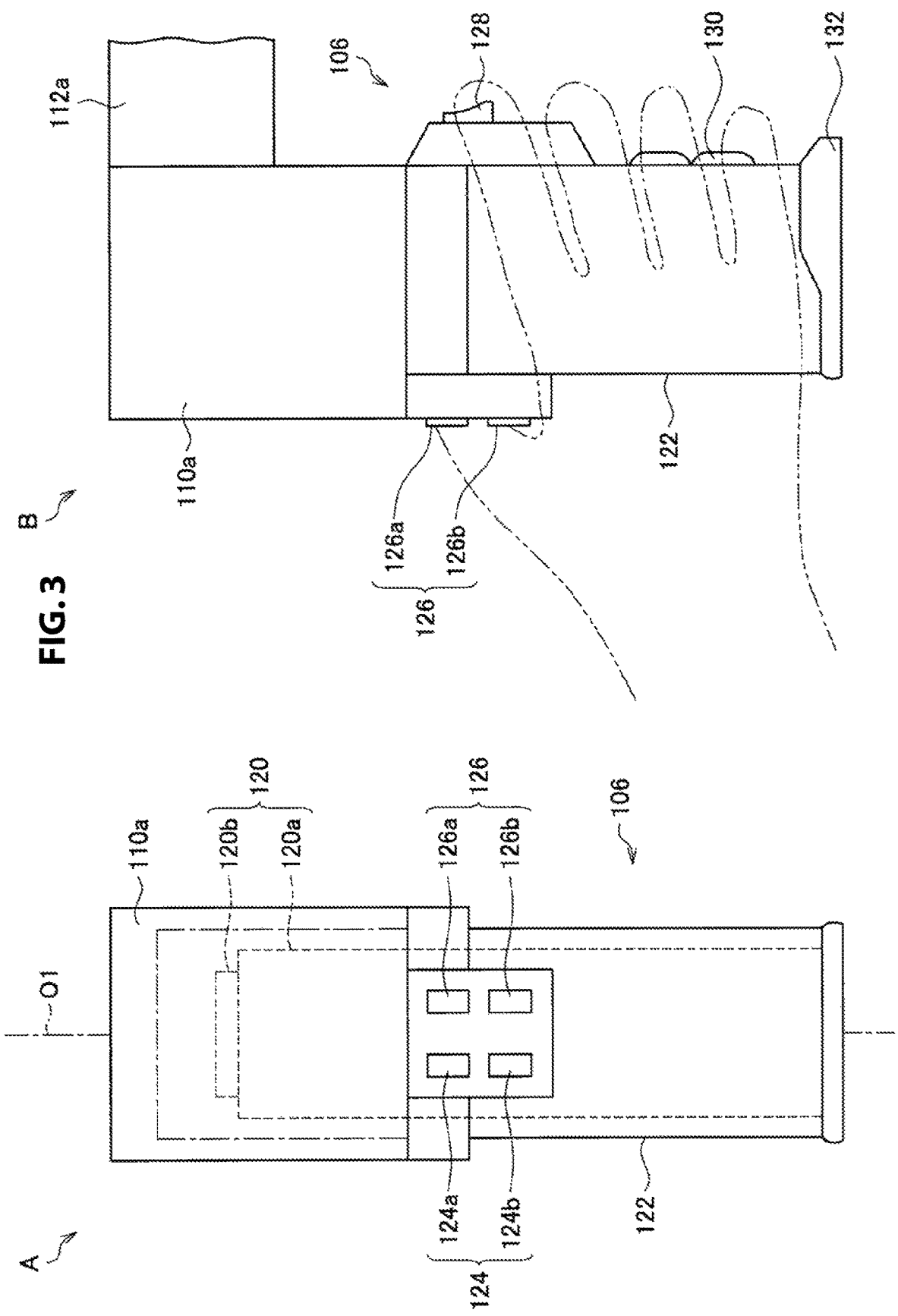
FIG. 3 is an explanatory diagram for explaining an example of the configuration of an imaging device provided in a medical observation apparatus according to the present embodiment.

FIG. 3 is an explanatory diagram for explaining an example of the configuration of the imaging device 106 provided in the medical observation apparatus 100 according to the present embodiment.

For example, the imaging device 106 includes an imaging member 120 and a barrel member 122 having an approximately cylindrical shape, with the imaging member 120 being provided inside the barrel member 122.

On an aperture on the bottom end of the barrel member 122 (the lower end in FIG. 3), for example, a cover glass (not illustrated) for protecting the imaging member 120 is provided.

Additionally, for example, a light source (not illustrated) is provided inside the barrel unit 122, and during imaging, the subject is irradiated with illuminating light radiating from the light source through the cover glass. Reflected light (observation light) from the subject irradiated with illuminating light enters the imaging member 120 through the cover glass (not illustrated), whereby an image signal indicating the subject (an image signal indicating a taken image) is obtained by the imaging member 120.

As the imaging member 120, any of various known types of configurations used in an electronic imaging microscope section can be applied.

To give one example, the imaging member 120 includes an optical system 120a and an image sensor 120b including an imaging element that takes an image of an observation target with light transmitted through the optical system 120a, for example. The optical system 120a includes optical elements such as a mirror and one or multiple lenses, such as an objective lens, a zoom lens, and a focus lens, for example. Examples of the image sensor 120b include an image sensor using multiple imaging elements, such as a complementary metal-oxide semiconductor (CMOS) or a charge-coupled device (CCD).

The imaging member 120 may also include a pair of imaging elements, or in other words, be configured to function as what is called a stereo camera. The imaging member 120 is equipped with one or multiple functions typically provided in an electronic imaging microscope section, including at least a zoom function (one or both of an optical zoom function and an electronic zoom function), such as an autofocus (AF) function.

In addition, the imaging member 120 may also be configured to be capable of imaging at what are called high resolutions, such as 4K and 8K, for example. By configuring the imaging member 120 to be capable of imaging at high resolutions, it becomes possible to ensure a predetermined resolution (such as full HD image quality, for example), while also displaying an image on the display apparatus 200 having a large display screen, such as 50 inches or more, for example. For this reason, visibility is improved for the surgeon watching the display screen. Also, by configuring the imaging member 120 to be capable of imaging at high resolutions, even if the taken image is enlarged by the electronic zoom function and displayed on the display screen of the display apparatus 200, it is still possible to ensure a predetermined resolution. Furthermore, in the case of using the electronic zoom function to ensure a predetermined resolution, since it is possible to reduce the performance of the optical zoom function in the imaging device 106, the optical system of the imaging device 106 can be simplified, and the imaging device 106 can be configured more compactly.

In the imaging device 106, for example, various operating devices for controlling the operation of the imaging device 106 are provided. For example, in FIG. 3, a zoom switch 124, a focus switch 126, and an operating mode change switch 128 are provided on the imaging device 106. Note that the positions and shapes in which to provide the zoom switch 124, the focus switch 126, and the operating mode change switch 128 obviously are not limited to the example illustrated in FIG. 3.

The zoom switch 124 and the focus switch 126 are an example of an operating device for adjusting the imaging parameters in the imaging device 106.

The zoom switch 124 includes, for example, a zoom-in switch 124a that increases the zoom magnification (enlargement ratio), and a zoom-out switch 124b that decreases the zoom magnification. By performing an operation on the zoom switch 124, the zoom magnification is adjusted, and the zoom is adjusted.

The focus switch 126 includes, for example, a long-range focus switch 126a that increases the focal length to the observation target (subject), and a close-range focus switch 126b that decreases the focal length to the observation target. By performing an operation on the focus switch 126, the focal length is adjusted, and the focus is adjusted.

The operating mode change switch 128 is an example of an operating device for changing the operating mode of the arm 104 in the imaging device 106. By performing an operation on the operating mode change switch 128, the operating mode of the arm 104 is changed. Examples of operating modes of the arm 104 include a locked mode and a free mode, as described above.

One example of an operation with respect to the operating mode change switch 128 is an operation of pressing the operating mode change switch 128. For example, the operating mode of the arm 104 becomes the free mode while the surgeon is pressing the operating mode change switch 128, and the operating mode of the arm 104 becomes the locked mode when the surgeon is not pressing the operating mode change switch 128.

In addition, the imaging device 106 is provided with, for example, an anti-slip member 130 and a projecting member 132 in order to further raise operability, convenience, and the like when an operator who performs operations on various operation devices performs an operation.

The anti-slip member 130 is a member provided to prevent slipping of an operating body such as a hand when, for example, the operator performs an operation on the barrel member 122 with the operating body. The anti-slip member 130 is formed with a material having a large coefficient of friction, for example, and has a slip-resistant structure due to unevenness or the like.

The projecting member 132 is member provided to prevent an operating body such as a hand blocking the field of view of the optical system 120a when the operator performs an operation on the barrel member 122 with the operating body, or to prevent a cover glass (not illustrated) from becoming dirty due to the cover glass being contacted by the operating body when an operation is performed with the operating body.

Note that the position and shape in which each of the anti-slip member 130 and the projecting member 132 is provided obviously are not limited to the example illustrated in FIG. 3. In addition, the imaging device 106 does not have to be provided with one or both of the anti-slip member 130 and the projecting member 132.

The image signal (image data) generated by imaging in the imaging device 106 is subjected to image processing in a processor that functions as the control section described later, for example. Examples of image processing according to the present embodiment include one or multiple processes from among various processes such as gamma correction, white balance adjustment, image enlargement or reduction related to the electronic zoom function, and pixel interpolation, for example. Note that in the case in which the medical observation system according to the present embodiment includes a control apparatus (not illustrated)

that controls various operations in the medical observation apparatus 100, the image processing according to the present embodiment may also be performed in the control apparatus (not illustrated).

For example, the medical observation apparatus 100 transmits a display control signal and the image signal subjected to imaging processing as above to the display apparatus 200.

By transmitting the display control signal and the image signal to the display apparatus 200, on the display screen of the display apparatus 200, a medical captured image in which the observation target is imaged (for example, a taken image in which the operating site is imaged) is displayed enlarged or reduced at a desired magnification by one or both of the optical zoom function and the electronic zoom function.

The medical observation apparatus 100 includes the hardware configuration illustrated with reference to FIGS. 1 and 3, for example.

Note that the hardware configuration of the medical observation apparatus according to the present embodiment is not limited to the configuration illustrated with reference to FIGS. 1 and 3.

For example, the medical observation apparatus according to the present embodiment may also be a configuration not provided with the base 102, in which the arm 104 is directly attached to the ceiling, a wall, or the like of the operating room or the like. For example, in the case in which the arm 104 is attached to the ceiling, the medical observation apparatus according to the present embodiment becomes a configuration in which the arm 104 hangs down from the ceiling.

Also, although FIG. 1 illustrates an example configured so that six degrees of freedom are realized with respect to the driving of the imaging device 106, the configuration of the arm 104 is not limited to a configuration whereby the degrees of freedom with respect to the driving of the imaging device 106 become six degrees of freedom. For example, it is sufficient to configure the arm 104 so that the imaging device 106 can move appropriately in accordance with the application, and factors such as the number and arrangement of joint sections and links, and the directions of the drive shafts of the joint sections can be set appropriately so that the arm 104 has the desired degrees of freedom.

Also, although FIGS. 1 and 3 illustrate an example in which various types of operating devices for controlling the operation of the imaging device 106 are provided on the imaging device 106, some or all of the operating devices illustrated in FIGS. 1 and 3 may also not be provided on the imaging device 106. To give one example, the various types of operating devices for controlling the operation of the imaging device 106 may also be provided in another part other than the imaging device 106 included in the medical observation apparatus according to the present embodiment. Also, to give another example, the various types of operating devices for controlling the operation of the imaging device 106 may also be external operating devices, such as a footswitch or a remote controller.

[2] Medical Sterile Cover According to Present Embodiment

Next, the medical sterile cover according to the present embodiment will be described.

Hereinafter, a medical sterile cover capable of covering an electronic imaging medical observation apparatus like the medical observation apparatus 100 illustrated in FIG. 1 will be given as an example of the medical sterile cover according to the present embodiment. Note that the medical observation apparatus to be covered by the medical sterile cover according to the present embodiment is not limited to an electronic imaging medical observation apparatus, and the medical sterile cover according to the present embodiment may also cover an optical medical observation apparatus.

[2-1] Overview of Medical Sterile Cover According to Present Embodiment

As described above, if a site whose sterile state is not ensured, such as the face or head of a medical personnel member, comes into contact with a part covered by an existing medical sterile cover, the medical personnel member may need to re-cover the optical medical observation apparatus or electronic imaging medical observation apparatus with a new medical sterile cover. Also, even in the case in which a tool or the like whose sterile state is not ensured comes into contact with a part covered by an existing medical sterile cover, the medical personnel member similarly may need to re-cover the optical medical observation apparatus or electronic imaging medical observation apparatus with a new existing medical sterile cover. Also, as described above, the situation of re-covering with a new medical sterile cover may lead to reduced surgical efficiency, and in addition, increased costs due to the use of a new medical sterile cover are a concern.

In contrast, the medical sterile cover according to the present embodiment has a layered structure in which a "covering member that covers the medical observation apparatus to ensure the sterile state of the medical observation apparatus" is multiply layered, and also includes a "detachment section enabling the layered covering member to be detached layer by layer".

In the case in which a site whose sterile state is not ensured on a medical personnel member (or a tool or the like whose sterile state is not ensured; the same applies hereinafter) comes into contact with a part covered by the medical sterile cover according to the present embodiment, if the medical personnel member detaches the covering member whose sterile state is not ensured, the medical sterile cover according to the present embodiment can be returned to the sterile state.

Herein, the medical sterile cover according to the present embodiment includes a detachment section enabling the covering member to be detached layer by layer. Thus, the medical personnel member is able to detach the covering member whose sterile state is not ensured more easily and rapidly than re-covering the medical observation apparatus with a new medical sterile cover.

Consequently, through the use of the medical sterile cover according to the present embodiment, in the case in which a site whose sterile state is not ensured on a medical personnel member comes into contact with the medical sterile cover, a more rapid return to the sterile state can be realized. Also, through the use of the medical sterile cover according to the present embodiment, even in the case in which a tool or the like whose sterile state is not ensured comes into contact with the medical sterile cover, similarly, a more rapid return to the sterile state can be realized.

Note that in the case in which the medical observation apparatus included in the medical observation system 1000 is an electronic imaging medical observation apparatus as illustrated in FIG. 1, a user who uses the electronic imaging medical observation apparatus (for example, a medical personnel member such as a surgeon or a surgeon's assistant) is not required to peer into an eyepiece lens included in an optical microscope like in the case of using an optical medical observation apparatus, and thus it is possible to move the position of the imaging device more freely. For this reason, in the case in which the medical observation apparatus included in the medical observation system 1000 is an electronic imaging medical observation apparatus, the possibility of a site whose sterile state is not ensured on a medical personnel member making contact with the sterile region is conceivably higher than the case in which the medical observation apparatus included in the medical observation system 1000 is an optical medical observation apparatus.

As described above, in the case in which the medical sterile cover according to the present embodiment is used, a more rapid return to the sterile state can be realized, and thus even in surgery performed using an electronic imaging medical observation apparatus, such as microsurgery, for example, the risk of the surgery being interrupted can be minimized.

[2-2] Configuration of Medical Sterile Cover According to Present Embodiment

Hereinafter, an example of the configuration of the medical sterile cover according to the present embodiment will be described. Note that the configuration of the medical sterile cover according to the present embodiment obviously is not limited to the example indicated below.

[2-2-1] Medical Sterile Cover According to First Embodiment

Figure 4:
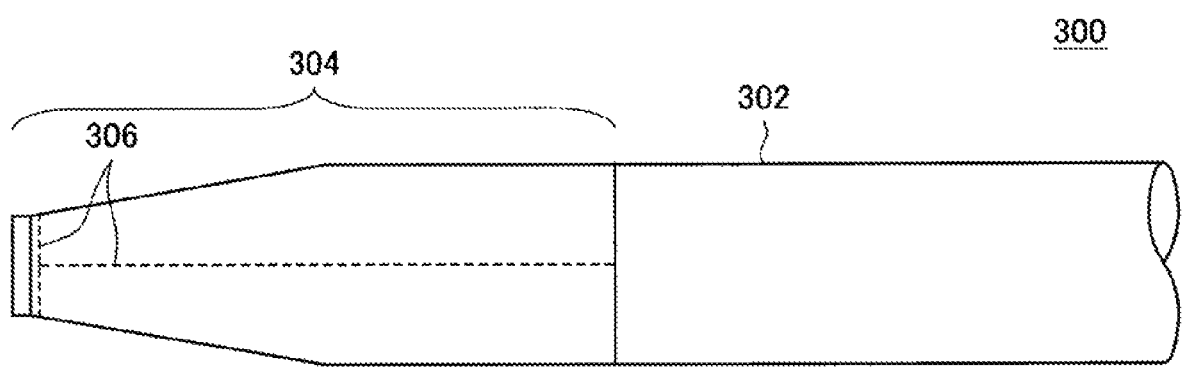
FIG. 4 is an explanatory diagram illustrating an example of the configuration of a medical sterile cover according to a first embodiment.
Figure 5:
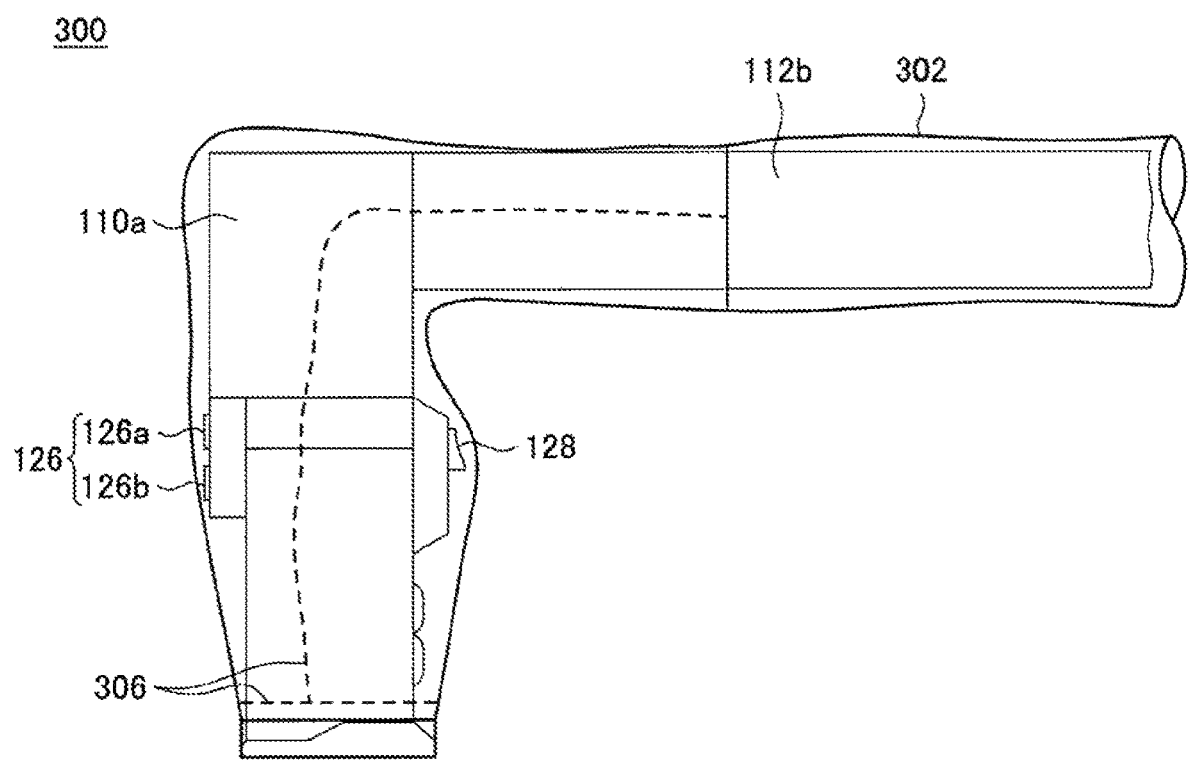
FIG. 5 is an explanatory diagram illustrating an example of the configuration of a medical sterile cover according to the first embodiment.

FIGS. 4 and 5 are explanatory diagrams illustrating an example of the configuration of the medical sterile cover according to the first embodiment. FIG. 4 illustrates a portion of a medical sterile cover 300 in the case of not covering the medical observation apparatus 100. FIG. 5 illustrates an example of the case in which the medical sterile cover 300 illustrated in FIG. 4 is covering the medical observation apparatus 100. Hereinafter, FIGS. 4 and 5 will be referenced as appropriate to describe the configuration of the medical sterile cover 300 according to the first embodiment.

The medical sterile cover 300 includes a covering member 302 that covers the medical observation apparatus 100 to ensure the sterile state of the medical observation apparatus 100, and has a layered structure 304 in which multiple covering members 302 are layered. The number of the covering members 302 included in the layered structure 304 may be two, and may also be three or more. The number of the covering members 302 included in the layered structure 304 is set in consideration of the manufacturing costs and the like of the medical sterile cover 300, for example.

In the case in which the medical sterile cover 300 covers the medical observation apparatus 100, the covering member 302 covers all of the medical observation apparatus 100, or a portion of the medical observation apparatus 100, for example. The portion of the medical observation apparatus 100 covered by the covering member 302 may be, for example, "the imaging device 106 and the entirety of the arm 104", or "the imaging device 106 and a portion of the arm 104".

The part covered by the medical sterile cover 300 becomes the sterile region. In other words, the case in which the covering member 302 covers a portion of the medical observation apparatus 100 is a case in which it is not necessary to treat the entire medical observation apparatus 100 as the sterile region, for example.

In addition, the covering member 302 has a shape corresponding to the object to cover. To give one example, in the case in which the covering member 302 covers a portion of the medical observation apparatus 100, the covering member 302 is tubular to correspond with the imaging device 106 and the arm 104, for example. Also, in the case in which the covering member 302 covers the entire medical observation apparatus 100, the covering member 302 is shaped like a bag large enough to cover the entire medical observation apparatus 100, for example. Note that the shape of the covering member 302 obviously is not limited to the examples indicated above.

For example, as illustrated in FIG. 4, in the medical sterile cover 300, a portion of the medical sterile cover 300 is the layered structure 304. In other words, the covering member 302 of the lowermost layer among the covering members 302 included in the layered structure 304 covers a broader range than the covering members 302 of the other layers.

The portion of the medical sterile cover 300 where the layered structure 304 is provided may be a "part corresponding to the imaging device 106 and a portion of the arm 104", as illustrated in FIG. 5, for example.

Herein, the "part corresponding to the imaging device 106 and a portion of the arm 104" refers to a part narrower than the part in which the covering member 302 of the lowermost layer covers the medical observation apparatus 100. In other words, the range over which the layered structure 304 covers the medical observation apparatus 100 is narrower than the range over which the covering member 302 of the lowermost layer covers the medical observation apparatus 100.

The "part corresponding to the imaging device 106 and a portion of the arm 104" may be, for example, "the imaging device 106, and the part of the arm 104 up to the links 112*a* and 112*b*", "the imaging device 106, and the part of the arm 104 up to a portion of the links 112*a* and 112*b*" as illustrated in FIG. 5, or the like.

The part where the layered structure 304 is provided in the medical sterile cover 300 is set arbitrarily during the design stage, the manufacturing stage, or the like of the medical sterile cover 300, in consideration of a "site that easily comes into contact with a part whose sterile state is not ensured on a medical personnel member in the case in which the medical sterile cover 300 is used (that is, in the case in which the medical sterile cover 300 covers the medical observation apparatus 100)", for example.

For example, as illustrated in FIG. 4, by providing the layered structure 304 in a portion of the medical sterile cover 300, advantageous effects like the following are exhibited, for example.

The cost of the medical sterile cover 300 can be reduced.

In the case in which a site whose sterile state is not ensured on a medical personnel member comes into contact with the medical sterile cover 300, since the range over which the medical personnel member detaches the covering member 302 is smaller, an even more rapid return to the sterile state can be realized.

Note that the entire medical sterile cover 300 may also be configured as the layered structure 304.

The medical sterile cover 300 additionally includes a detachment section 306 that detaches the covering members 302 included in the layered structure 304 layer by layer.

The detachment section 306 is formed in the part of the covering member 302 corresponding to the layered structure 304. The detachment section 306 formed in the covering member 302 may be, for example, perforations formed in the covering member 302 as illustrated in FIGS. 4 and 5.

By including the detachment section 306 as illustrated in FIGS. 4 and 5, a medical personnel member is able to peel off the covering member 302 in the uppermost layer of the layered covering members 302 along the perforations, and thereby detach the layered covering members 302 layer by layer.

Figure 6:
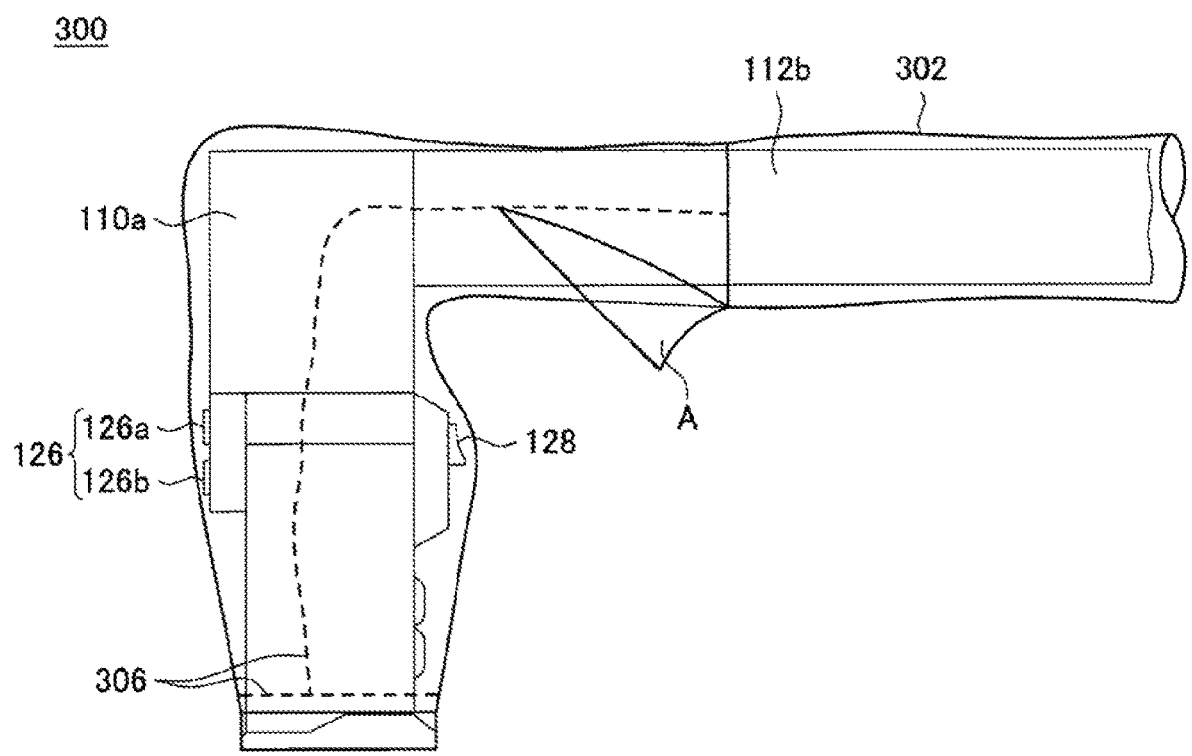
FIG. 6 is an explanatory diagram illustrating an example of the configuration of a medical sterile cover according to the first embodiment.

FIG. 6 is an explanatory diagram illustrating an example of the configuration of the medical sterile cover 300 according to the first embodiment, and illustrates an example in which, in the medical sterile cover 300 illustrated in FIG. 5, the covering member 302 in the uppermost layer of the covering members 302 included in the layered structure 304 is being detached.

In the case in which a site whose sterile state is not ensured on a medical personnel member comes into contact with the medical sterile cover 300, the medical personnel member peels off the covering member 302 in the uppermost layer of the layered covering members 302 along the perforations (one example of the detachment section 306) formed in the covering member 302, as illustrated by A of FIG. 6, for example.

Thus, in the medical sterile cover 300, the sterile state is secured again, and a rapid return to the sterile state is realized.

The medical sterile cover 300 according to the first embodiment has the configuration illustrated with reference to FIGS. 4 to 6, for example.

Herein, the medical sterile cover 300 includes the layered structure 304 in which covering members 302 are layered, and perforations (one example of the detachment section 306) formed in the covering member 302. Thus, as illustrated by A of FIG. 6, for example, if a medical personnel member peels off the covering member 302 in the uppermost layer of the layered covering members 302 along the perforations formed in the covering member 302, the covering member 302 can be returned to the sterile state.

Consequently, through the use of the medical sterile cover 300, a medical personnel member is able to restore the sterile state of the medical sterile cover 300 easily and quickly.

[2-2-2] Medical Sterile Cover According to Second Embodiment

Figure 7:
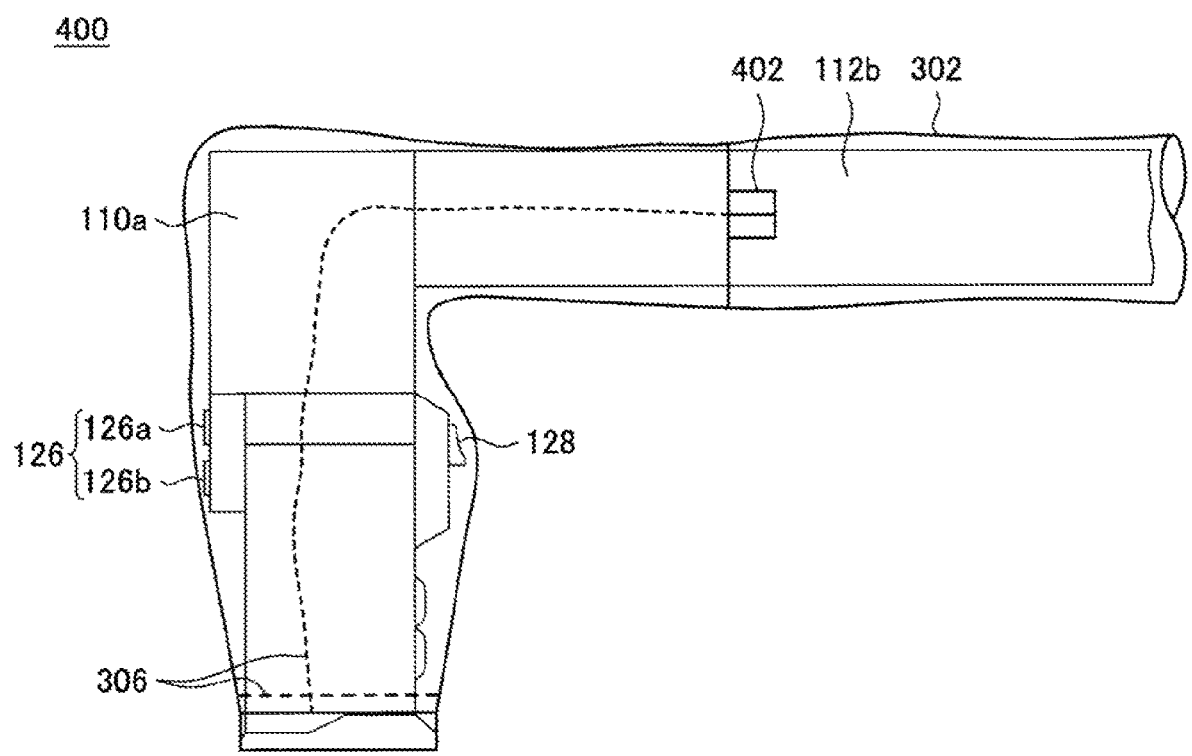
FIG. 7 is an explanatory diagram illustrating an example of the configuration of a medical sterile cover according to a second embodiment.

FIG. 7 is an explanatory diagram illustrating an example of the configuration of the medical sterile cover 400 according to the second embodiment. FIG. 7 illustrates an example of the case in which the medical sterile cover 400 is covering the medical observation apparatus 100.

The medical sterile cover 400 has a configuration that is basically similar to the medical sterile cover 300 according to the first embodiment illustrated in FIGS. 4 to 6 (including configurations according to modifications of the medical sterile cover 300). The difference between the medical sterile cover 400 and the medical sterile cover 300 illustrated in FIGS. 4 to 6 is that "the medical sterile cover 400 additionally includes a detachment assistance member 402".

The detachment assistance member 402 is an example of a member that assists with the detachment of the covering member 302 by the detachment section 306. For example, the detachment assistance member 402 is provided on the covering member 302 of each layer included in the layered structure 304. Note that the detachment assistance member 402 may also not be provided on the covering member 302 in the lowermost layer.

The detachment assistance member 402 may be, for example, detaching tape affixed to one end of the detachment section 306. Note that the detachment assistance member 402 is not limited to detaching tape, and may also be an arbitrary member capable of carrying out the detachment of the detachment assistance member 402 by the detachment section 306 when held by a person detaching the covering member 302.

In the case in which a site whose sterile state is not ensured on a medical personnel member comes into contact with the medical sterile cover 400, the medical personnel member, while holding the detaching tape (one example of the detachment assistance member 402; the same applies hereinafter), peels off the covering member 302 in the uppermost layer of the layered covering members 302 along the perforations (one example of the detachment section 306) formed in the covering member 302.

Thus, in the medical sterile cover 400, the sterile state is secured again, and a rapid return to the sterile state is realized.

The medical sterile cover 400 according to the second embodiment has the configuration illustrated in FIG. 7, for example.

Herein, the medical sterile cover 400 has a configuration that is basically similar to the medical sterile cover 300 according to the first embodiment illustrated in FIGS. 4 to 6.

Consequently, through the use of the medical sterile cover 400, advantageous effects similar to the advantageous effects exhibited in the case of using the medical sterile cover 300 according to the first embodiment are exhibited.

Also, since a medical personnel member is able to detach the covering member 302 while holding the detaching tape, in the case of using the medical sterile cover 400, the sterile state of the medical sterile cover 400 can be restored more easily than in the case of using the medical sterile cover 300 illustrated in FIGS. 4 to 6.

[2-2-3] Medical Sterile Cover According to Third Embodiment

Figure 8:
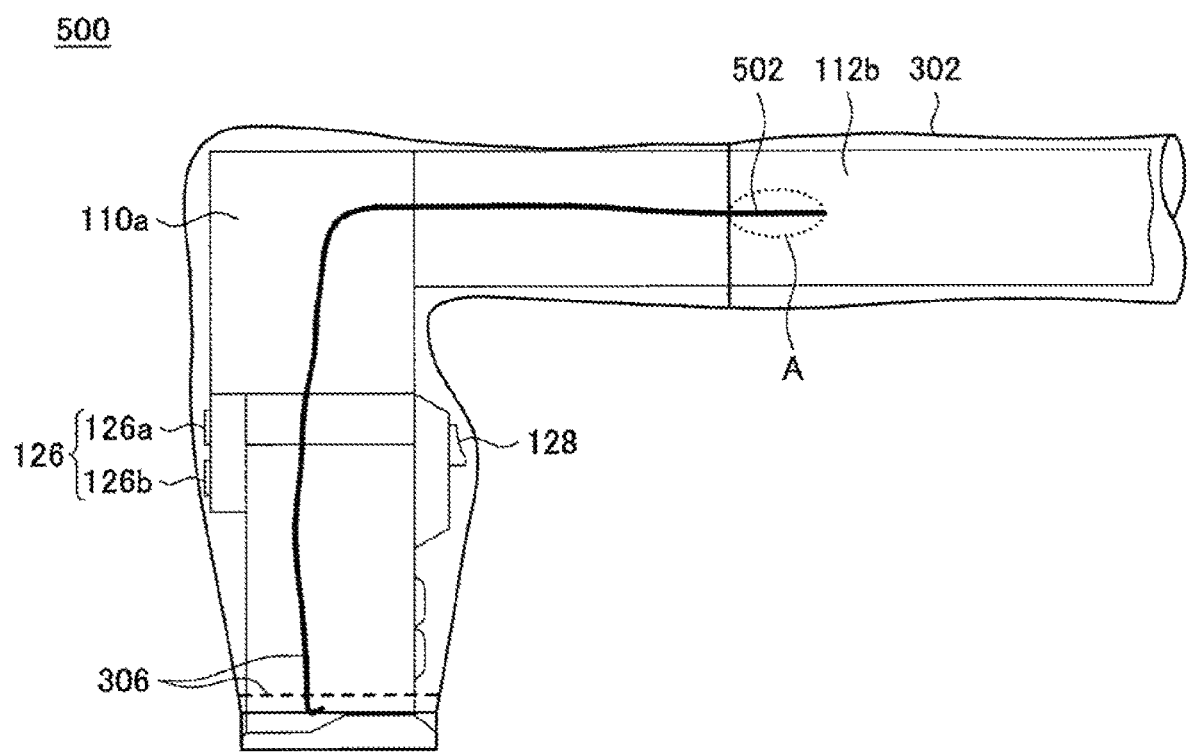
FIG. 8 is an explanatory diagram illustrating an example of the configuration of a medical sterile cover according to a third embodiment.

FIG. 8 is an explanatory diagram illustrating an example of the configuration of the medical sterile cover 500 according to the third embodiment. FIG. 8 illustrates an example of the case in which the medical sterile cover 500 is covering the medical observation apparatus 100.

The medical sterile cover 500 has a configuration that is basically similar to the medical sterile cover 300 according to the first embodiment illustrated in FIGS. 4 to 6 (including configurations according to modifications of the medical sterile cover 300). The difference between the medical sterile cover 500 and the medical sterile cover 300 illustrated in FIGS. 4 to 6 is that "the medical sterile cover 500 additionally includes a detachment assistance member 502".

The detachment assistance member 502 is another example of a member that assists with the detachment of the covering member 302 by the detachment section 306. For example, the detachment assistance member 502 is provided on the covering member 302 of each layer included in the layered structure 304. Note that the detachment assistance member 502 may also not be provided on the covering member 302 in the lowermost layer.

The detachment assistance member 502 may be, for example, a string-like member disposed along the detachment section 306 formed in the covering member 302. Note that the detachment assistance member 502 is not limited to a string-like member, and may also be a member of arbitrary shape capable of carrying out the detachment of the detachment assistance member 402 by the detachment section 306 when held by a person detaching the covering member 302.

As illustrated by A of FIG. 8, one end of the string-like member (one example of the detachment assistance member 502; the same applies hereinafter) is exposed to the outside of the medical sterile cover 500 from the end of the layered structure 304.

In the case in which a site whose sterile state is not ensured on a medical personnel member comes into contact with the medical sterile cover 500, the medical personnel member, while holding the string-like member, peels off the covering member 302 in the uppermost layer of the layered covering members 302 along the perforations (one example of the detachment section 306) formed in the covering member 302.

Thus, in the medical sterile cover 500, the sterile state is secured again, and a rapid return to the sterile state is realized.

The medical sterile cover 500 according to the third embodiment has the configuration illustrated in FIG. 8, for example.

Herein, the medical sterile cover 500 has a configuration that is basically similar to the medical sterile cover 300 according to the first embodiment illustrated in FIGS. 4 to 6.

Consequently, through the use of the medical sterile cover 500, advantageous effects similar to the advantageous effects exhibited in the case of using the medical sterile cover 300 according to the first embodiment are exhibited.

Also, since a medical personnel member is able to detach the covering member 302 while holding the string-like member, in the case of using the medical sterile cover 500, the sterile state of the medical sterile cover 500 can be restored more easily than in the case of using the medical sterile cover 300 illustrated in FIGS. 4 to 6.

Furthermore, in the medical sterile cover 500, since the string-like member is disposed along the perforations (one example of the detachment section 306) formed in the covering member 302, the perforations can be torn off by the string-like member. In other words, with the string-like member, the effect of assisting with the detachment of the covering member 302 is higher than the detaching tape included in the medical sterile cover 400 according to the second embodiment illustrated in FIG. 7. Thus, in the case of using the medical sterile cover 500, a medical personnel member is able to detach the covering member 302 more easily than in the case of using the medical sterile cover 400 illustrated in FIG. 7.

[2-2-4] Medical Sterile Cover According to Fourth Embodiment

Figure 9:
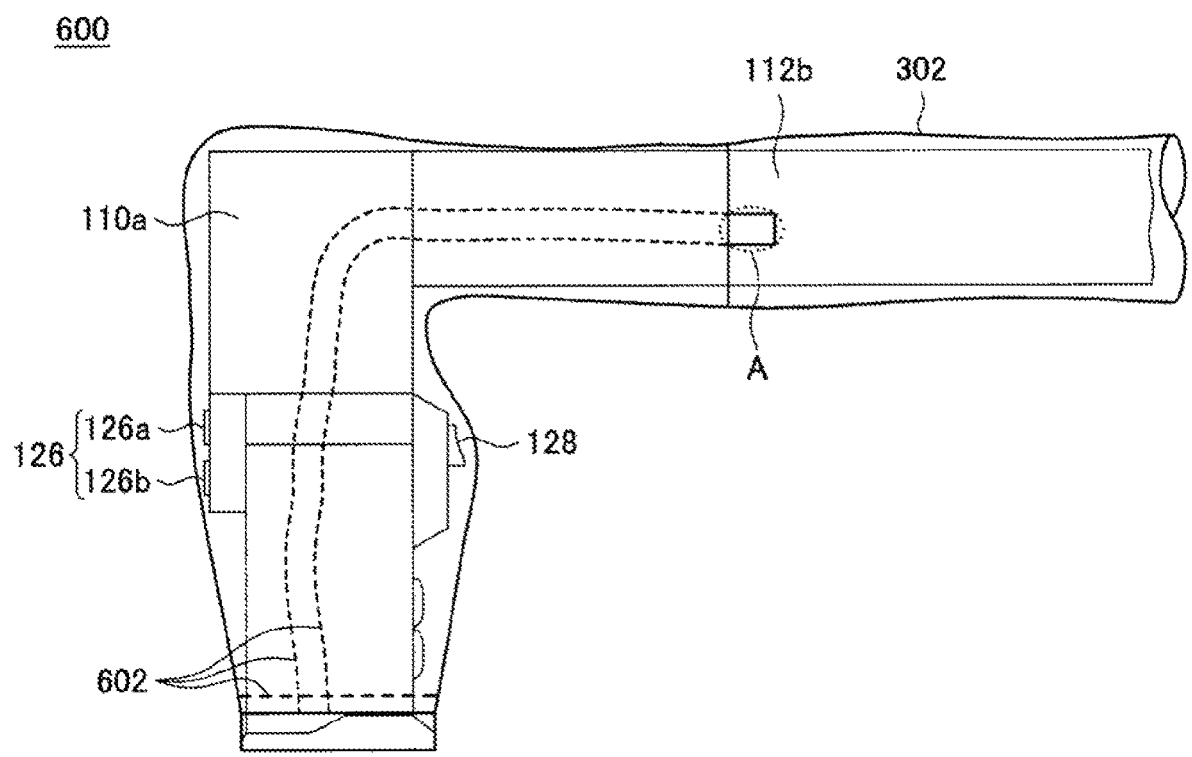
FIG. 9 is an explanatory diagram illustrating an example of the configuration of a medical sterile cover according to a fourth embodiment.

FIG. 9 is an explanatory diagram illustrating an example of the configuration of the medical sterile cover 600 according to the fourth embodiment. FIG. 9 illustrates an example of the case in which the medical sterile cover 600 is covering the medical observation apparatus 100.

The medical sterile cover 600 has a configuration that is basically similar to the medical sterile cover 300 according to the first embodiment illustrated in FIGS. 4 to 6 (including configurations according to modifications of the medical sterile cover 300). The difference between the medical sterile cover 600 and the medical sterile cover 300 illustrated in FIGS. 4 to 6 lies in a detachment section 602 included in the medical sterile cover 600.

Similarly to the detachment section 306 illustrated in FIGS. 4 to 6, the detachment section 602 is formed in the part of the covering member 302 corresponding to the layered structure 304. One difference between the detachment section 602 illustrated in FIG. 9 and the detachment section 306 included in the medical sterile cover 300 illustrated in FIGS. 4 to 6 is that the detachment section 602 includes two sets of perforations formed approximately parallel. Herein, approximately parallel according to the present embodiment means, for example, "the two sets of formed perforations are strictly parallel", and "the angle obtained by straight lines corresponding to each of the two sets of formed perforations is of a magnitude that can be considered parallel inside the range in which the detachment section 602 is formed in the covering member 302".

Also, as illustrated by A of FIG. 9, a portion of the detachment section 602 may also be exposed to the outside of the medical sterile cover 600 from the end of the layered structure 304. The part of the detachment section 602 exposed to the outside as illustrated by A of FIG. 9 fulfills the role of a detachment assistance member. Note that obviously a portion of the detachment section 602 may also not be exposed to the outside.

By having the configuration illustrated in FIG. 9, for example, the detachment section 602 functions like a tear-away tab provided on the cellophane wrapping of a box of sweets or the like, for example.

In the case in which a site whose sterile state is not ensured on a medical personnel member comes into contact with the medical sterile cover 600, the medical personnel member, while holding the portion of the detachment section 602 exposed to the outside, peels off the covering member 302 in the uppermost layer of the layered covering members 302 along the two perforations (one example of the detachment section 306) formed approximately parallel in the covering member 302.

Thus, in the medical sterile cover 600, the sterile state is secured again, and a rapid return to the sterile state is realized.

The medical sterile cover 600 according to the fourth embodiment has the configuration illustrated in FIG. 9, for example.

Herein, the medical sterile cover 600 has a configuration that is basically similar to the medical sterile cover 300 according to the first embodiment illustrated in FIGS. 4 to 6.

Consequently, through the use of the medical sterile cover 600, advantageous effects similar to the advantageous effects exhibited in the case of using the medical sterile cover 300 according to the first embodiment are exhibited.

Also, since the detachment section 602 includes two sets of perforations formed approximately parallel in the covering member 302, for example, the initial tearaway part when the perforations are torn is wider than the initial tearaway part in the case of a single set of perforations. Thus, in the case of using the medical sterile cover 600, a medical personnel member's hand finds a grip easily when peeling off the covering member 302, and thus the work efficiency of the medical personnel member can be improved.

[2-3] Example of Advantageous Effects Exhibited by Use of Medical Sterile Cover According to Present Embodiment By using the medical sterile cover according to the present embodiment, the advantageous effects indicated below are exhibited, for example. Note that the advantageous effects exhibited by using the medical sterile cover according to the present embodiment obviously are not limited to the example indicated below.

During surgery, even in the case in which the surgeon accidentally comes into contact with the medical sterile cover according to the present embodiment with a site whose sterile state is not ensured, such as one's head, the surgeon is able to restore the sterile state easily, without re-covering with a new medical sterile cover.

Since the sterile state can be restored more easily than re-covering with a new medical sterile cover, the risk of the surgery being interrupted can be minimized.

It should be understood by those skilled in the art that various modifications, combinations, sub-combinations and alterations may occur depending on design requirements and other factors insofar as they are within the scope of the appended claims or the equivalents thereof.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1) A medical sterile cover including:
a layered structure in which a plurality of covering members that cover a medical observation apparatus to ensure a sterile state of the medical observation apparatus is layered; and
a detachment section configured to detach the layered plurality of covering members layer by layer.

(2) The medical sterile cover according to (1), in which
a portion of the medical sterile cover has the layered structure.

(3) The medical sterile cover according to (2), in which
the medical observation apparatus is provided with an imaging device, and an arm supporting the imaging device and including a plurality of links joined to each other by one or a plurality of joint sections, and
the portion of the medical sterile cover is a part corresponding to the imaging device and a portion of the arm.

(4) The medical sterile cover according to any one of (1) to (3), in which
the detachment section is formed in the plurality of covering members.

(5) The medical sterile cover according to (4), in which
the detachment section is perforations formed in the plurality of covering members.

(6) The medical sterile cover according to (5), in which
two sets of the perforations are formed approximately parallel.

(7) The medical sterile cover according to any one of (1) to (6), further including:
a detachment assistance member configured to assist with the detachment of the plurality of covering members by the detachment section.

(8) The medical sterile cover according to (7), in which
the detachment assistance member is detaching tape affixed to one end of the detachment section.

(9) The medical sterile cover according to (7), in which
the detachment assistance member is a string-like member disposed along the detachment section formed in the plurality of covering members.

(10) The medical sterile cover according to any one of (1) to (9), in which
the plurality of covering members is tubular.

(11) A medical observation apparatus including:
an arm including a plurality of links joined to each other by one or a plurality of joint sections;
an imaging device supported by the arm; and
a medical sterile cover, in which
the medical sterile cover includes
a layered structure in which a plurality of covering members that cover the imaging device and at least a portion of the arm to ensure a sterile state of the covered part is layered, and
a detachment section configured to detach the layered plurality of covering members layer by layer.

What is claimed is:

1. A medical sterile cover, comprising:
a layered structure covering at least a portion of a medical observation apparatus to ensure a sterile state of the medical observation apparatus, wherein each layer of the layered structure is a covering member,
wherein each covering member includes a detachment section, wherein each covering member of the layered structure is individually removeable from the layered structure via the detachment section.

2. The medical sterile cover according to claim 1, wherein a predetermined portion of each covering member is removable based on the detachment section.

3. The medical sterile cover according to claim 2, wherein the medical observation apparatus is provided with an imaging device, and an arm supporting the imaging device and including a plurality of links joined to each other by one or a plurality of joint sections, and
the predetermined portion of the medical sterile cover is a part corresponding to the imaging device and a portion of the arm.

4. The medical sterile cover according to claim 1, wherein the detachment section is formed into each covering member.

5. The medical sterile cover according to claim 4, wherein the detachment section is perforations formed into each covering member.

6. The medical sterile cover according to claim 5, wherein two sets of the perforations are formed approximately parallel.

7. The medical sterile cover according to claim 1, further comprising:
a detachment assistance member configured to assist with the detachment of the plurality of covering members by the detachment section.

8. The medical sterile cover according to claim 7, wherein the detachment assistance member is detaching tape affixed to one end of the detachment section.

9. The medical sterile cover according to claim 7, wherein the detachment assistance member is a string-like member disposed along the detachment section.

10. The medical sterile cover according to claim 1, wherein
each covering member is tubular.

11. A medical observation apparatus comprising:
an arm including a plurality of links joined to each other by one or a plurality of joint sections;
an imaging device supported by the arm; and
a medical sterile cover, wherein
the medical sterile cover includes
a layered structure covering the imaging device and at least a portion of the arm to ensure a sterile state of the imaging device, wherein each layer of the layered structure is a covering member,
wherein each covering member includes a detachment section, wherein each covering member of the layered structure is individually removable from the layered structure via the detachment section.

* * * * *